US010154786B2

(12) United States Patent
Fischer et al.

(10) Patent No.: US 10,154,786 B2
(45) Date of Patent: Dec. 18, 2018

(54) ELECTROSURGICAL INSTRUMENT COMPRISING A LIGHT GUIDE

(71) Applicant: Erbe Elektromedizin GmbH, Tuebingen (DE)

(72) Inventors: Klaus Fischer, Nagold (DE); Alexander Neugebauer, Moessingen (DE); Dominik Spether, Freiburg (DE); Markus Enderle, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 138 days.

(21) Appl. No.: 14/304,518

(22) Filed: Jun. 13, 2014

(65) Prior Publication Data

US 2014/0378960 A1   Dec. 25, 2014

(30) Foreign Application Priority Data

Jun. 20, 2013   (EP) .................................... 13173066

(51) Int. Cl.
*A61B 18/12*   (2006.01)
*A61B 5/00*   (2006.01)
(Continued)

(52) U.S. Cl.
CPC .......... *A61B 5/0084* (2013.01); *A61B 5/0075* (2013.01); *A61B 18/1477* (2013.01);
(Continued)

(58) Field of Classification Search
CPC ...... A61B 18/1477; A61B 2018/00607; A61B 2018/00904; A61B 2018/00982;
(Continued)

(56) References Cited

U.S. PATENT DOCUMENTS 4,637,392 A * 1/1987 Sorochenko ........... A61B 18/14
606/50
5,085,499 A * 2/1992 Griffin ................... G01N 21/69
356/311

(Continued)

FOREIGN PATENT DOCUMENTS

JP   S61-500769   4/1986
JP   2002-532186 A   10/2002
(Continued)

OTHER PUBLICATIONS

Notice of Reasons for Rejection in corresponding Japanese Application No. 2014-123307, dated May 19, 2015, 7 pages.
(Continued)

*Primary Examiner* — Daniel Fowler
(74) *Attorney, Agent, or Firm* — Fitch, Even, Tabin & Flannery LLP

(57) ABSTRACT

The instrument according to the invention for electrosurgically impacting biological tissue comprises an electrode (18) as well as a light guide (21), which is connected to a light inlet window (19), which is formed by means of a fluid body (27). The light guide is connected to a light analysis device (13), so as to absorb the light, which is generated at the electrode (18) in response to the HF surgery and so as to supply it to the light analysis device (13). The light inlet window (19) is arranged at the point of origin of the light, namely immediately at the electrode, that is, at the spark, which is generated. An adulteration of the absorbed light by means of smoke or particle deposition on the light inlet window (19) can virtually be avoided.

13 Claims, 3 Drawing Sheets

(51) Int. Cl.
*A61B 18/00* (2006.01)
*A61B 18/14* (2006.01)

(52) U.S. Cl.
CPC ............... *A61B 2018/00607* (2013.01); *A61B 2018/00904* (2013.01); *A61B 2018/00982* (2013.01); *A61B 2018/1435* (2013.01); *A61B 2218/002* (2013.01)

(58) Field of Classification Search
CPC ...... A61B 2018/1435; A61B 2218/002; A61B 5/0075; A61B 5/0084
See application file for complete search history.

(56) References Cited

U.S. PATENT DOCUMENTS

| | | | | |
|---|---|---|---|---|
| 5,169,395 | A * | 12/1992 | Narciso, Jr. | A61N 5/062 606/14 |
| 5,769,791 | A | 6/1998 | Benaron et al. | |
| 5,845,646 | A * | 12/1998 | Lemelson | A61B 17/32075 128/899 |
| 6,402,719 | B1 * | 6/2002 | Ponzi | A61B 18/24 604/528 |
| 6,723,094 | B1 * | 4/2004 | Desinger | A61B 18/14 606/41 |
| 2002/0026127 | A1 * | 2/2002 | Balbierz | A61B 18/1206 600/567 |
| 2003/0212394 | A1 * | 11/2003 | Pearson | A61B 18/1477 606/41 |
| 2004/0176761 | A1 | 9/2004 | Desinger | |
| 2007/0213704 | A1 | 9/2007 | Truckai et al. | |
| 2008/0119694 | A1 | 5/2008 | Lee | |
| 2012/0123397 | A1 | 5/2012 | Epshtein | |
| 2012/0296205 | A1 | 11/2012 | Chernov et al. | |
| 2012/0296238 | A1 | 11/2012 | Chernov et al. | |
| 2012/0316558 | A1 | 12/2012 | Hendriks et al. | |

FOREIGN PATENT DOCUMENTS

| | | |
|---|---|---|
| JP | 2008178668 A | 8/2008 |
| JP | 2012-522566 A | 9/2012 |
| WO | 2011055369 A2 | 5/2011 |

OTHER PUBLICATIONS

Notification of Reason for Refusal in corresponding Japanese application No. 2014-123307, dated Dec. 25, 2015, 3 pages.
Office action in corresponding Korean application No. 10-2014-0074437, dated Jan. 7, 2016, 6 pages.
Written Opinion in corresponding Korean application No. 10-2014-0074437, dated Aug. 21, 2015, 5 pages.
European Search Report in corresponding European application No. 14155440, dated Apr. 8, 2015, 5 pages.
European Search Report for corresponding application EP13173066.5, dated Nov. 28, 2013.
Notice of Reasons for Rejection in corresponding Japanese Application No. 2015-186564 dated Oct. 31, 2017, with Machine English Translation (7 pages).

* cited by examiner

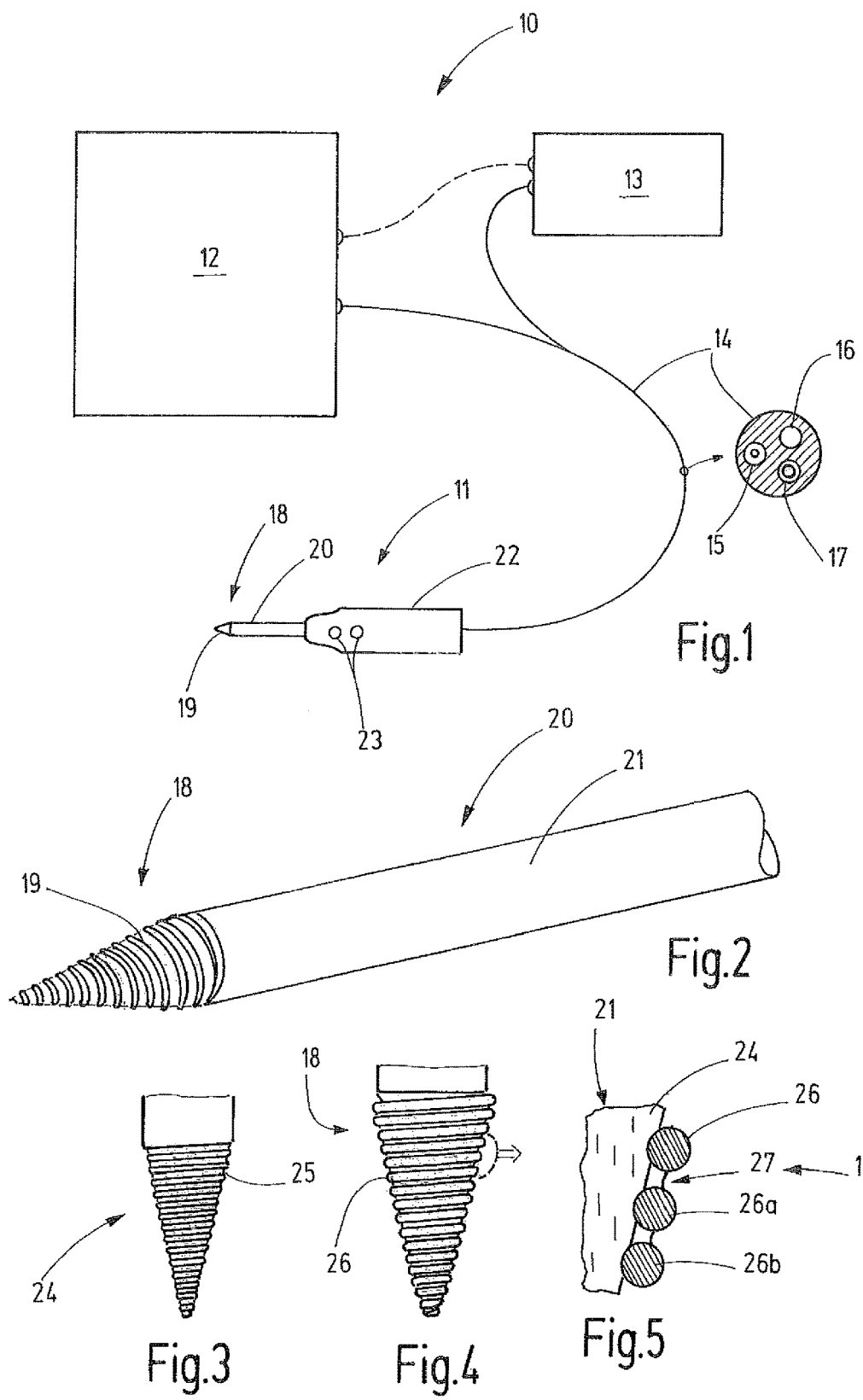

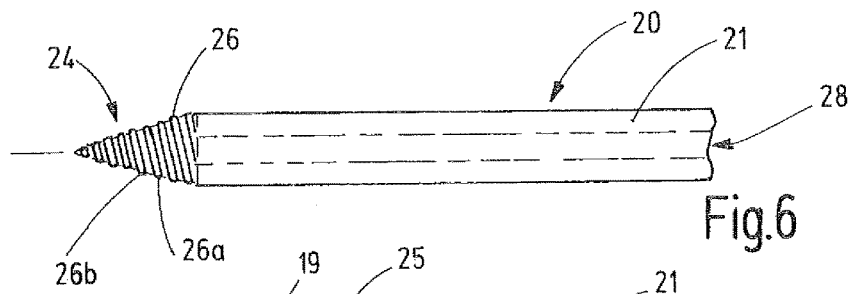
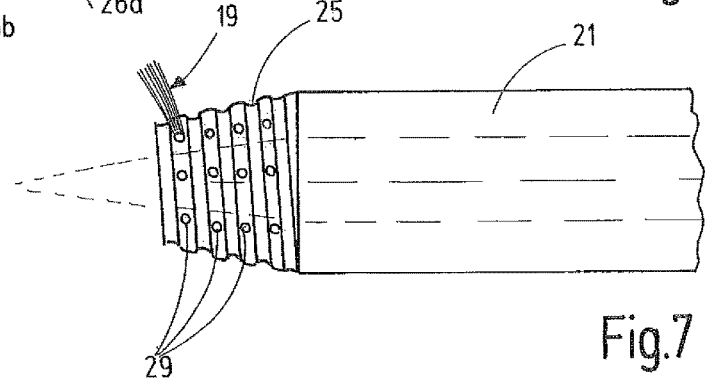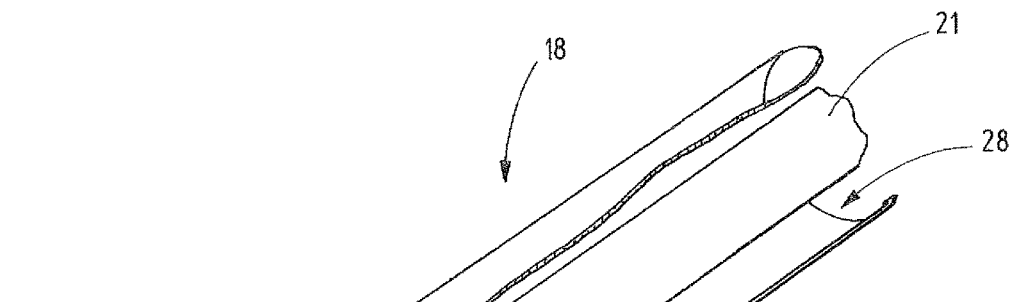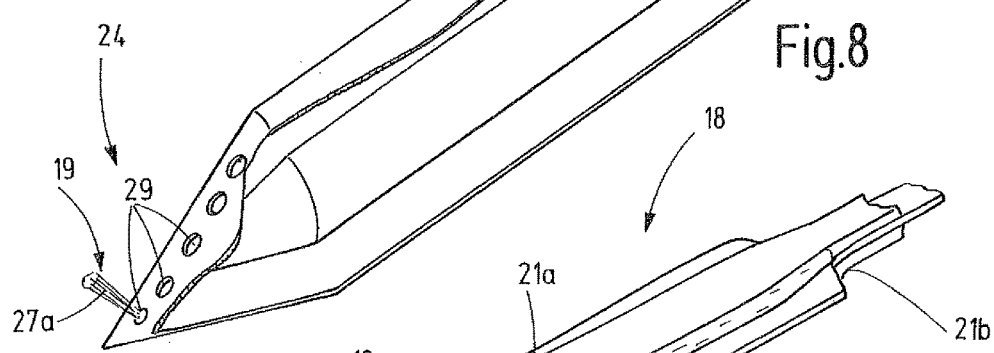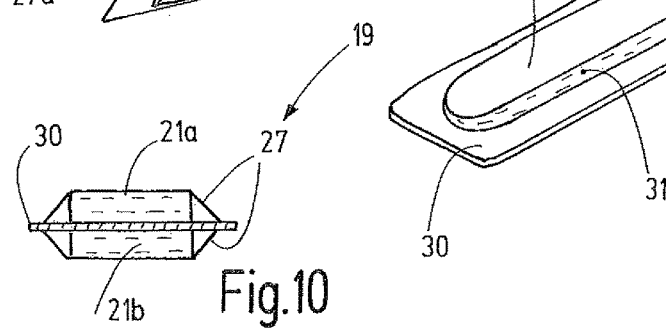

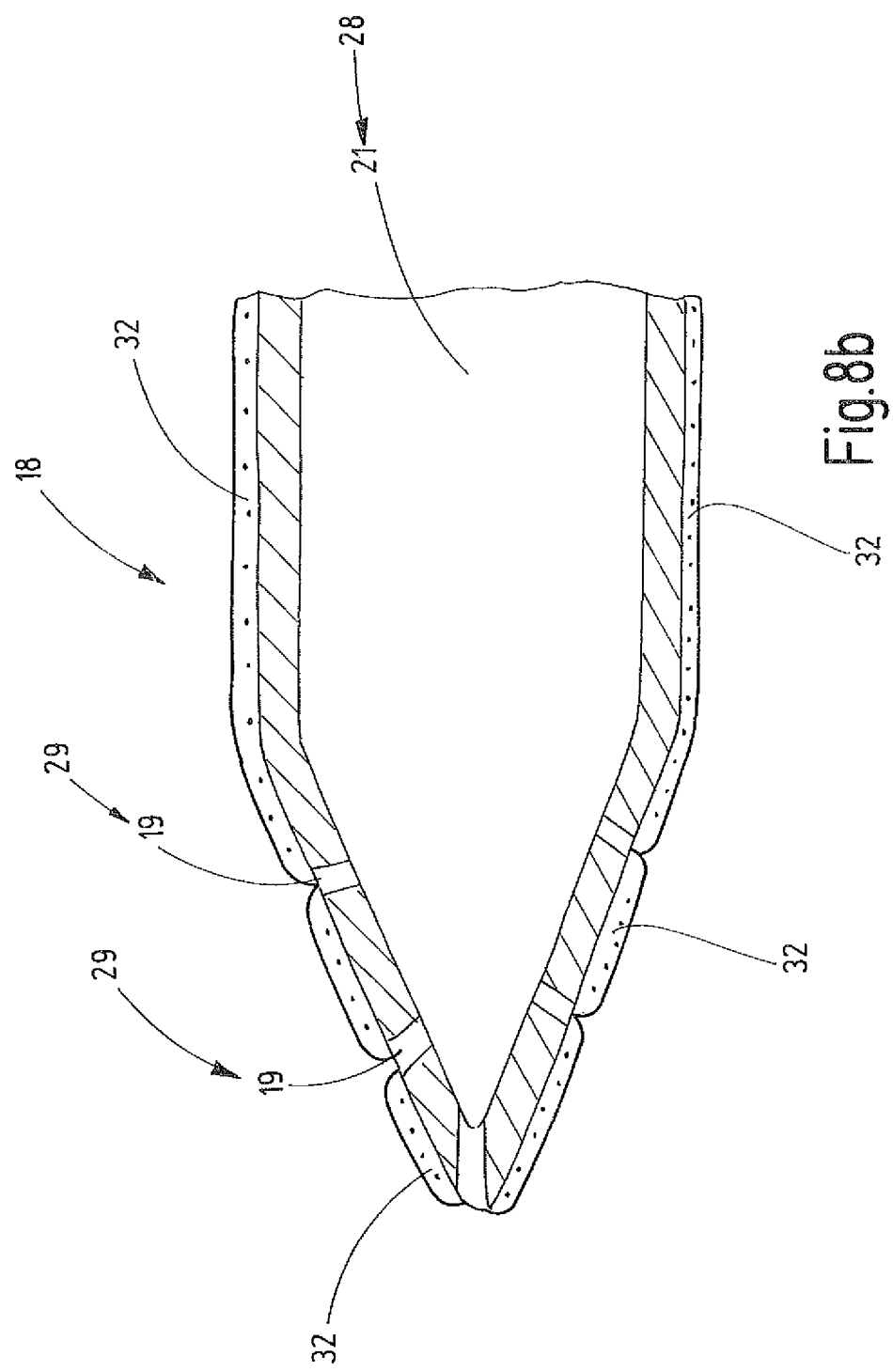

ELECTROSURGICAL INSTRUMENT COMPRISING A LIGHT GUIDE

RELATED APPLICATION(S)

This application claims the benefit of European Patent Application No. EP13173066.5 filed Jun. 20, 2013, the contents of which are incorporated herein by reference as if fully rewritten herein.

TECHNICAL FIELD

The invention relates to an instrument for electrosurgically impacting biological tissue and in particular to an instrument for HF surgery.

BACKGROUND

Electrosurgical instruments are known, which impact biological tissue by generating sparks and which supply the light generated thereby to an analysis device.

For this purpose, WO 2011/055369 A2 discloses a micro plasma head for medical applications. This micro plasma head is formed by means of an elongated flexible instrument, at the end of which provision is made for electrodes for generating plasma. A light guide, the open front surface of which forms a light inlet window, ends so as to be slightly recessed. A plasma, the light of which is absorbed by the light inlet window, forms in front of the light inlet window. The connected light analysis device examines the light spectrum of the light emanating from the plasma in particular for the presence of a characteristic phosphor line. This serves for the differentiation of living tissue of plaques in response to the use of the instrument for removing plaques in blood vessels.

A more subtle light examination is proposed by U.S. 2007/0213704 A1. The elongated instrument illustrated therein encompasses an optical fiber in the center, which ends in a spherical recess of a ceramic end piece. Two sharp-edged electrodes, which generate a plasma in this recess, are also arranged in this recess.

A successful spectral light analysis requires for the light to reach to the spectral analyzer.

SUMMARY

The instrument according to the invention encompasses at least one electrode, which can be connected or which is connected to an electric source via a line. The source can be an HF generator, e.g. The electrode can be monopolar and can consists of one or a plurality of parts. In this case, the counter electrode, which is required to close an electric circuit, is fastened to the patient as neutral electrode.

The instrument can be embodied as an instrument for the use in open surgeries or as instrument, which is provided for laparoscopic use. It is set up in particular for HF surgical procedures, in the case of which sparks, advantageously with a spectrum of between 200 nm and 1200 nm, are generated at the electrode. Preferably, provision is made in such cases for an HF generator as electric source.

The instrument according to the invention is provided for connection to a light analysis device, by means of which information relating to the biological tissue, which is seized by the spark, are obtained from features of the absorbed light. To absorb this light, provision is made for a light inlet window, which is formed by means of a fluid body. The latter is in contact with the light guide, so as to transfer the absorbed light into the light guide and via the latter to the light analysis device. The fluid body has a liquid surface, which does not get dirty or char from the deposition of smoke particles, even if it is located in the immediate vicinity of the spark. It is thus possible to absorb the light, which emanates from the spark, without spectral distortion.

In particular when the light inlet window is arranged in the immediate vicinity of the electrode, it can be ensured that the light, which emanates from the spark, is actually absorbed and is not covered by tissue parts located between the spark and the light inlet window, by smoke or the like. In the preferred case, the light inlet window can be arranged so as to touch the electrode, for example in that a fluid body is held by means of adhesion between the electrode and the light guide. For this purpose, it is advantageous, if the light inlet window and/or the electrode encompass a hydrophilic surface. A substantially resting fluid body can be held in this manner between a surface of the light guide and the electrode. In the preferred case, two hydrophilic electrode surface, which are located opposite one another and between which there is no potential difference, form a gap, the bottom of which is formed by a hydrophilic light guide surface. The gap width is preferably so small that the fluid body is held in the gap by means of capillary effect. The fluid, which forms the fluid body, can be rinsing fluid, which is present in the vicinity, lymph or also a fluid, which is supplied via a channel. The channel can extend through the light guide, for example.

The light inlet window can also be formed by means of a flowing fluid body, for example in that a transparent liquid jet escapes from the electrode. For example, the light guide can be arranged in a fluid channel, which leads fluid to the fluid outlet openings, from which fluid jets then escape. They form the light inlet windows and guide light, which originates from the spark, into the fluid channel, where it is further absorbed by the light guide.

Regardless of whether the fluid body, which forms the light inlet window, is provided so as to rest or flow, it is advantageous, when the electrode encompasses at least two areas, which are electrically connected to one another and between which the light inlet window is arranged. The fluid body can thus be arranged between the electrode surfaces, which have the same potential, in the most immediate vicinity of the spark, which is generated.

In the case of a particularly preferred embodiment, the instrument encompasses a light guide comprising a rigid section, which supports the electrode. The rigid section can merge into a tapering tip, for example, at which an electrode is arranged, which consists of one or of a plurality of wires, metal strips or the like. The angle of the tapering tip can be between 5 and 90 degrees, for example. The size of the angle is then determined as a function of the refraction index of the used light guide, e.g. in response to the use of glass with 1.46 and as a function of the refraction index of the surrounding medium of the light guide, such as air (1.0) or water (1.33).

Preferably, the electrode is formed by means of a wire, which envelopes the tapering tip in a plurality of windings. A fluid body can remain in the gaps between adjacent windings by means of adhesion and capillary effect, if applicable. Said fluid body forms the light inlet window and transfers light to the light guide. Regardless of the location, at which location of the cone-shaped wire windings a spark originates, a majority of the light, which is generated, is absorbed by the light guide and can thus be supplied to the analysis device in an unadulterated manner. For example, the light guide can be embodied by means of a light-guiding material, such as glass, plastic, e.g. The light guide can also consists of a suitable pipe or cannula, which is metal-coated on the inside and which, as an alternative, can be filled with standing or flowing fluid. Further details of advantageous embodiments of the invention are the subject matter of the drawing, of the description or of claims.

BRIEF DESCRIPTION OF THE DRAWINGS

FIG. 1 shows an electrosurgical device comprising an instrument according to the invention, in schematized illustration, FIG. 2 shows a light-guiding electrode of the instrument according to FIG. 1, in simplified perspective illustration, FIG. 3 shows an end of a light guide for setting up a light-guiding electrode, in side view, FIG. 4 shows the end of the electrode according to FIG. 2, in side view, FIG. 5 shows a sectional illustration of the tip of the electrode according to FIG. 4, in enlarged sectional illustration, FIG. 6 shows a modified embodiment of a light-guiding electrode comprising a fluid channel, FIG. 7 shows the light-guiding support for the electrode according to FIG. 6, in schematized side view, FIG. 8 shows an embodiment for an electrode comprising escaping fluid jets as light inlet window, in particular sectional perspective illustration, FIG. 8b shows an embodiment of an electrode according to FIG. 8, which is coated with an insulating material, in sectional illustration, FIG. 9 shows a further modified embodiment of an electrode according to the invention comprising a light guide, in perspective illustration and FIG. 10 shows the electrode according to FIG. 9, in cross section.

DETAILED DESCRIPTION

FIG. 1 illustrates an electrosurgical device 10, which includes an instrument 11, which is to be guided by the user, a feeding device 12 and a light analysis device 13. As illustrated, it can be embodied as a separate unit or also as a part of the device 12. To connect the instrument 11 to the device 12 and to the light analysis device 13, provision is made for corresponding lines 14, which include at least one electric line 15, a light guide 16 and optionally at least one fluid line 17. The electric line 15 connects an electrode 18 of the instrument 11 to the feeding device 12, which includes an HF generator, for example. The light guide 16 connects a light inlet window 19, which is provided at the electrode 18, to the light analysis device 13.

The instrument 11 can be embodied as laparoscopic instrument or also, as illustrated symbolically in FIG. 1, as instrument for open surgical procedures. It encompasses an electrode support 20, which is illustrated separately in FIG. 2. Said electrode support is formed, for example, by means of a rigid light guide 21, which is connected to the light guide 16 of the line 14. The connection can be realized within a handle 22, which can also support one or a plurality of operating elements 23, or which can be realized so as to be spaced apart from said handle. As is illustrated in FIG. 3, the electrode support, which is formed by the rigid light guide 21, can be embodied so as to be tapered in a cone-shaped manner at one end 24. At this end 24, a one-start or multi-start spiral groove 25 can be embodied, the lead of which is larger than the width of a wire, which is to be accommodated by the spiral groove 25. FIG. 4 illustrates a wire 26, which forms the electrode 18 and which is inserted into the spiral groove 25 so as to be wound in a helical manner. This wire 26 forms the actual electrode. It is connected to the line 15 via one or a plurality of wires, which extend along the rigid light guide 21.

The relationships are illustrated one again separately in FIG. 5. A distance exists between adjacent windings 26a, 26b of the wire 26, so that the light guide 21 or its end 24, respectively, remains visible at that location. Preferably, the surface of the light guide is embodied in a hydrophilic manner. In addition, the surface of the wire 26 is preferably embodied in a hydrophilic manner, at least in the part, which adjoins the light guide 21. This means that the part of the light guide 21, which is exposed between the windings of the wire 26, and the adjoining parts of the wires 26 are wetted slightly by water and hold a water body by means of adhesion.

It is illustrated in FIG. 5 that a fluid body 27 is held between adjacent windings of the wire 26 by means of adhesion. If the gap between the windings 26a, 26b is sufficiently narrow, it can also be said that there is a capillary effect. Due to the circular cross section of the wire 26, the gap also widens towards the light guide.

The hydrophilic characteristic of the surfaces, which are touched by the fluid body 27, can be seen by means of the concave curve of its surface, which is directed outwardly. The fluid body 27 consists substantially of water, for example rinsing liquid, lymph or the like. Said fluid body forms the light inlet window 19, via which the light of a spark, which emanates from the wire 26, is absorbed and is transferred to the light guide 21.

The case at hand pertains to a resting fluid body 27, which is formed by means of liquid, which flows from the environment. Smoke or other solid matter particles cannot stay permanently on its liquid surface. During operation, it is thus ensured that the light, which emanates from a spark, reaches the light analysis device 13 in an unadulterated manner. "Light" thereby does not only refer to visible light, but, if desired, also to infrared light and/or ultraviolet light.

The electrosurgical device 10, which was described in this respect, operates as follows:

The user uses the instrument 11, so as to carry out electrosurgical, preferably HF electrosurgical procedures. A neutral electrode, which is not illustrated in detail, which is connected to the device 12, is fastened to the patient. The user can now generate a spark to the tissue of a patient by means of the electrode 18 and can thus cause an effect, for example cutting, coagulating or the like. The light, which is generated by the spark, is influenced by the treated tissue in a subtle manner. Parts of the tissue, which are treated by the spark, molecules, molecule fragments, atoms, ions reach into the spark and generate a light emission. This light is absorbed via the light inlet window 19 and is supplied to the light analysis device 13 via the light guide 21, 16. Said light analysis device 13 carries out a spectral decomposition of the light and analyses the spectrum of the absorbed light, so as to determine the type of the treated tissue as precisely as possible. Corresponding signals, which can be seen, heard or felt by the practitioner, can then display the tissue type or a change of the tissue type.

It is pointed out that numerous modifications are possible. For example, the light analysis device 13 can be a part of the instrument 11. It can be installed in the handle 22 thereof, for example. Further modifications can relate to the electrode 18, the electrode support 20 and the fluid body 27. For this purpose, FIG. 6 illustrates an electrode support 20. The latter is preferably made of a light-guiding material. It thus forms the rigid light guide 21. In the rigid light guide 21, provision is made here for a fluid channel 28, through which a suitable fluid, for example a physiological salt solution, is guided to the end 24. Provision can be made at that location for one or preferably for a plurality of fluid outlet openings 29, which are connected to the fluid channel 28. The fluid outlet openings 29 are preferably arranged such that they empty between the windings 26a, 26b of the wire 26, which are spaced apart from one another, that is, such that they are located between the spiral groove 25, as is shown in FIG. 7.

In the case of such an instrument, the fluid body 27 can be renewed continuously via the fluid outlet openings 29 during the operation. It can also be effected as a function of the fluid pressure that fluid jets, which then act as light inlet window 19, escape from the fluid outlet openings 29. They are then connected directly to the sparks, which originate at the wire 26 and thus absorb the light thereof. In the case of this embodiment, it is also possible to use optically opaque material instead of the rigid light guide 21, and to arrange the light guide in the fluid channel 28, so as to absorb light from the fluid at that location.

It is pointed out that the rigid light guide 21 can also be embodied as flexible light guide in the case of all of the above-described embodiments according to FIGS. 1 to 7. This applies in particular for instruments 11, which are to be used laparoscopically.

A further embodiment of the instrument 11 according to the invention follows from FIG. 8. As a small thin-walled tube, the electrode 18 is embodied so as to be electroconductive or by means of partially applied electroconductive metal layers, at the end 24 of which fluid outlet openings 29 are embodied. Fluid, for example a physiological salt solution or another fluid, which is based on water, is guided to the fluid outlet openings 29 via the fluid channel 28. The fluid jets 27a, which escape at that location, form the light inlet windows 19. The fluid in the fluid channel 28 can form the light guide 21. In the event that the fluid pressure is less, so that the fluid only drips or seeps from the fluid outlet openings 29, the liquid-filled fluid outlet openings 29 form the light inlet windows 19.

The light guide 21, which preferably extends to the end 24, is arranged in the channel 28. It acts as light collector so as to capture the light, which reaches into the channel 28 via the fluid outlet openings 29, and to supply it to the light analysis device 13.

As is illustrated, the end 24 of the electrode 18 as well as the end of the light guide 21 can be formed in a cone-shaped manner, or also otherwise, if necessary, for example so as to be ball-shaped, spatulate or the like.

The light emission detection can be improved, when the spark is generated in the area of the light inlet windows 19. For this purpose, the exemplary embodiment according to FIG. 8 can encompass an electrically insulating layer, as is illustrated in FIG. 8b. The application of this electrically insulating layer, for example a plastic layer, onto the electrode 18 comprising openings, which form the light inlet windows 19, leads to different thicknesses of the insulation layer. In the edge area of the openings of the light inlet windows, an insulation layer comprising a smaller thickness is generated. These locations, which are covered with a thin layer, are preferably penetrated when applying a HF voltage in the range of between 1000 to 10000 Volts, whereby the spark between the tissue and the electrode is generated directly at the light inlet windows 19. It is thus possible to define the point of origin of the spark and thus of the light emission immediately at the edge in the area of the light inlet window 19. The path to the light guide 29 is as small as possible. The light emission determination can thus take place virtually without any losses.

FIG. 9 shows a further modified embodiment. The electrode 18 encompasses an electroconductive small flat plate 30, which is connected to the electric source. Light guides 21a, 21b, which consist of plastic, for example, and which are connected to the light analysis device 13, are arranged on at least one, preferably on both flat sides of the small plate 30. The light guide is visible on the narrow sides 31 of the light guides 21a, 21b, which tower above the small plate 30. The narrow sides 31, as well as the flat sides of the small plate 30, are preferably embodied so as to be hydrophilic, so that fluid bodies 27, which are held at the light guide 21a, 21b and the small plate 30 by means of adhesion and which form the light inlet windows 19, form during operation from lymph, rinsing liquid or the like. Provision can also be made for fluid supply agents, so as to generate the fluid body 27 specifically or so as to supplement and renew it continuously.

The instrument 11 according to the invention for electrosurgically impacting biological tissue comprises an electrode 18 as well as a light guide 21, which is connected to a light inlet window 19, which is formed by means of a fluid body 27. The light guide is connected to a light analysis device 13, so as to absorb the light, which is generated in response to HF surgery at the electrode 18, and so as to supply it to the light analysis device 13. The light inlet window 19 is arranged at the point of origin of the light, namely immediately at the electrode, that is, at the spark, which is generated. An adulteration of the absorbed light caused by smoke or particle deposition on the light inlet window 19 can virtually be avoided.

LIST OF REFERENCE NUMERALS 10 electrosurgical device
11 instrument
12 device
12 light analysis device
14 line
15 electric line
16 light guide
17 fluid line
18 electrode
19 light inlet window
20 electrode support
21 rigid light guide
22 handle
23 operating elements
24 end of the light guide 21
25 spiral groove
26 wire
26a, b wire windings, which form areas of the electrode 18
27 fluid body
27a flowing fluid body, escaping fluid jet
28 fluid channel
29 fluid outlet openings
30 small plate
31 narrow sides
32 insulating material, for example plastic

What is claimed is:
1. An instrument for electrosurgically impacting biological tissue, the instrument comprising:
an electrode (18) configured to connect to an electric source (12) via a line (15);

a light guide (21) comprising a light guiding fiber or rod, which is spaced from at least one light inlet window (19), and via which the instrument can be connected to a light analysis device (13), wherein the light inlet window (19) is formed by a fluid body (27);

wherein the light guide (21) is disposed in a channel (28) configured to convey fluid that forms the fluid body at the at least one light inlet window (19) such that the light guide (21) is at least partially surrounded by the fluid in the channel (28);

wherein the light guide (21) is spaced from the at least one light inlet window (19) by the fluid in the channel (28); and a fluid outlet opening (29) in the electrode in communication with the channel to allow the fluid in the channel to pass therethrough, wherein the light inlet window (19) is formed at least in part by the fluid body within the fluid outlet opening.

2. The instrument according to claim 1, wherein the light inlet window (19) is arranged in an immediate vicinity to the electrode (18).

3. The instrument according to claim 1, wherein the light inlet window (19) and/or the electrode (18) include a hydrophilic surface at least in sections.

4. The instrument according to claim 1, wherein the electrode (18) comprises at least two areas (26a, 26b), which are connected to one another electrically, between which the light inlet window (19) is arranged.

5. The instrument according to claim 1, wherein the light inlet window (19) is embodied so as to extend along the electrode (18, 26).

6. The instrument according to claim 1, wherein the light inlet window (19) is embodied by a resting fluid body (27) or by a flowing fluid body (27a).

7. The instrument according to claim 1, wherein the light guide (21) and the channel (28) together define a light path.

8. The instrument according to claim 1, wherein the light inlet window's (19) shape is formed by a fluid outlet opening (29), which is in fluid communication with the fluid channel (28).

9. The instrument according to claim 1, wherein the light guide (21) comprises a rigid section.

10. The instrument according to claim 1 further comprising the light analysis device (13) configured to receive and analyze light created by operation of the electrode and received via the at least one light inlet window (19) and the light guide (21).

11. The instrument according to claim 1, wherein the electrode (18) has a distal end, and the light guide (21) within the channel (28) is spaced from the distal end of the electrode.

12. A method of collecting light for a light analysis device, the method comprising:
 producing a light by operation of an electrode;
 receiving at least a portion of the light by a light inlet window formed by a fluid body supported by structure supporting the electrode;
 passing at least a portion of the received portion of the light via a light guide to a light analysis device.

13. The method of claim 12 further comprising:
 holding the fluid body by a capillary effect between the electrode and the fluid body.

* * * * *